United States Patent
Goto et al.

[11] Patent Number: 5,256,362
[45] Date of Patent: Oct. 26, 1993

[54] METHOD FOR PRODUCTION OF GRANULAR CYSTEAMINE HYDROCHLORIDE

[75] Inventors: Yuujiro Goto, Kawasaki; Akira Tamura, Kurashiki; Hiromi Yokoyama, Yokohama, all of Japan

[73] Assignee: Nippon Shokubai Co., Ltd., Osaka, Japan

[21] Appl. No.: 703,744

[22] Filed: May 21, 1991

Related U.S. Application Data

[63] Continuation-in-part of Ser. No. 552,137, Jul. 13, 1990, abandoned.

[30] Foreign Application Priority Data

| Jul. 14, 1989 | [JP] | Japan | 1-180181 |
| Aug. 14, 1989 | [JP] | Japan | 1-207858 |
| Aug. 15, 1989 | [JP] | Japan | 1-209597 |
| Aug. 15, 1989 | [JP] | Japan | 1-209601 |
| Sep. 11, 1989 | [JP] | Japan | 1-232720 |
| Sep. 12, 1989 | [JP] | Japan | 1-234733 |
| Sep. 13, 1989 | [JP] | Japan | 1-235564 |
| Sep. 14, 1989 | [JP] | Japan | 1-236859 |
| Sep. 18, 1989 | [JP] | Japan | 1-240169 |
| Sep. 18, 1989 | [JP] | Japan | 1-240170 |
| Jul. 3, 1990 | [JP] | Japan | 2-176635 |
| Jul. 3, 1990 | [JP] | Japan | 2-176636 |
| Apr. 25, 1991 | [JP] | Japan | 3-095370 |

[51] Int. Cl.$^5$ .................................. B29B 9/10
[52] U.S. Cl. .................................. 264/13; 425/6
[58] Field of Search ............... 264/13, 14, 140; 425/6

[56] References Cited

U.S. PATENT DOCUMENTS

| 3,208,101 | 9/1965 | Kaiser et al. | 425/6 |
| 3,702,748 | 11/1972 | Storb et al. | 264/13 X |
| 3,737,328 | 6/1973 | Schumann | 425/6 X |
| 4,156,495 | 5/1979 | Weinhold | 264/13 X |
| 4,279,579 | 7/1981 | Froeschke | 425/6 |
| 4,374,247 | 2/1983 | Osawa et al. | 548/146 |
| 4,418,030 | 11/1983 | Muller et al. | 264/142 |
| 4,507,500 | 3/1985 | Nakayama et al. | 564/340 |
| 4,559,000 | 12/1985 | Froeschke | 425/6 |
| 4,578,021 | 3/1986 | Schermutzki | 425/6 |
| 4,610,615 | 9/1986 | Froeschke | 425/8 |
| 4,795,604 | 1/1989 | Matsuzaki et al. | 264/144 |

FOREIGN PATENT DOCUMENTS

| 3025461 | 1/1981 | Fed. Rep. of Germany . |
| 3049196 | 7/1982 | Fed. Rep. of Germany . |
| 50-29444 | 9/1975 | Japan . |
| 55-17019 | 5/1980 | Japan . |
| 55-111459 | 8/1980 | Japan . |
| 57-53458 | 3/1982 | Japan . |
| 57-64661 | 4/1982 | Japan . |
| 57-64684 | 4/1982 | Japan . |
| 57-67555 | 4/1982 | Japan . |
| 57-88171 | 6/1982 | Japan . |
| 57-144252 | 9/1982 | Japan . |
| 57-144253 | 9/1982 | Japan . |
| 57-203057 | 12/1982 | Japan . |
| 60-56951 | 4/1985 | Japan . |

*Primary Examiner*—Mary Lynn Theisen
*Attorney, Agent, or Firm*—Burns, Doane, Swecker & Mathis

[57] ABSTRACT

Molded particles of cysteamine hydrochloride obtained by preparing cysteamine hydrochloride powder having a water content of not more than 1% by weight and compression molding said cysteamine hydrochloride under a pressure of not less than 50 atmospheres, and granules of cysteamine hydrochloride obtained by cooling and solidifying a molten cysteamine hydrochloride, and manufacture thereof.

14 Claims, 2 Drawing Sheets

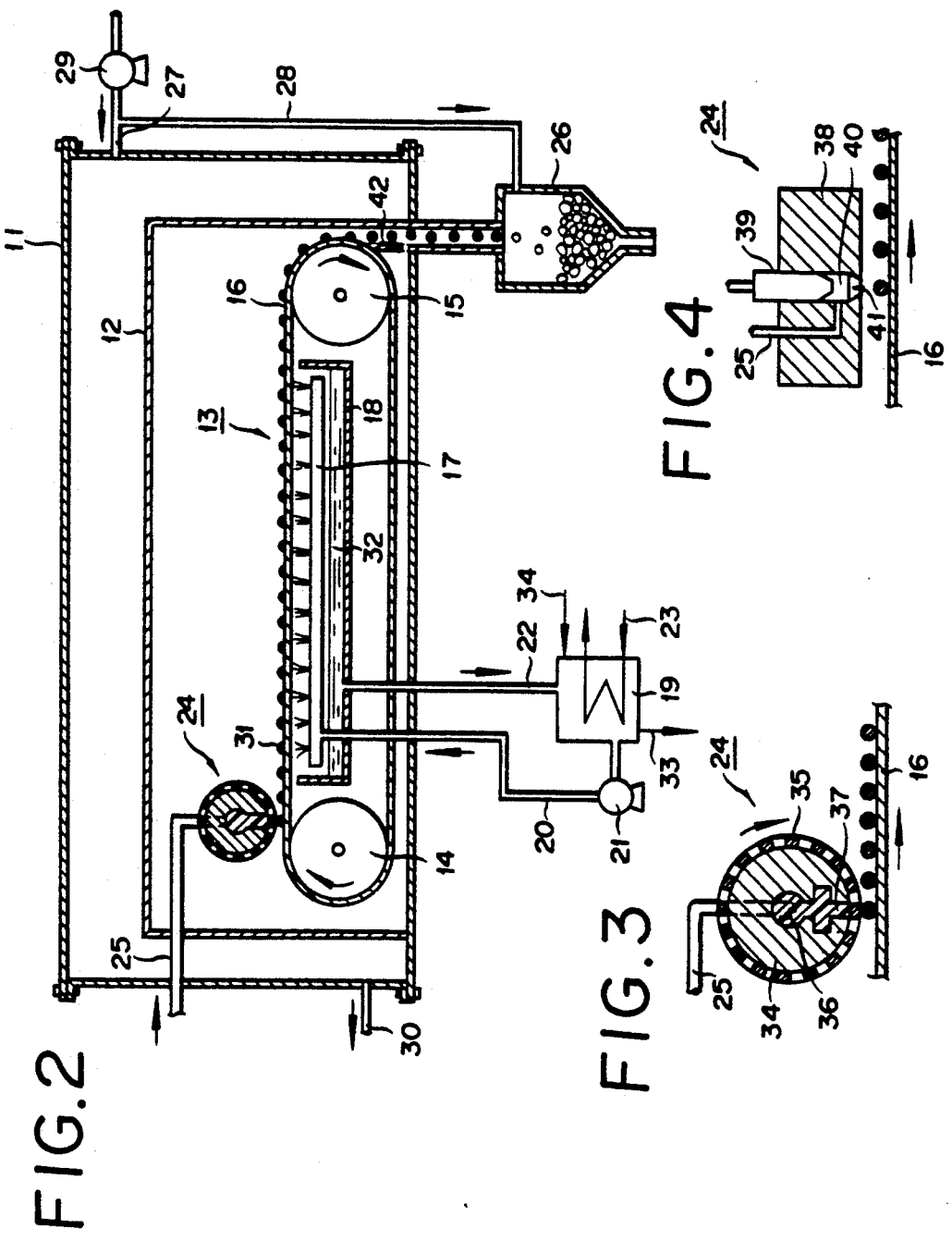

METHOD FOR PRODUCTION OF GRANULAR CYSTEAMINE HYDROCHLORIDE

This is a continuation-in-part of copending application Ser. No. 552,137, filed Jul. 13, 1990, which is now abandoned.

BACKGROUND OF THE INVENTION

1. Field of the Invention:

This invention relates to granular cysteamine hydrochloride and a method for the production thereof. More particularly, it relates to granules of cysteamine hydrochloride sparingly productive of very minute particles and highly uniform in particle size, excellent in operational efficiency of handling as evidenced by unsusceptibility to agglomeration while in storage, and also excellent in solubility in inorganic acids and organic liquids and a method for the production thereof.

2. Description of the Prior Art:

Cysteamine hydrochloride is a useful compound as a raw material on for example medicines and agricultural pesticides.

Heretofore, the cysteamine hydrochloride has been generally produced by any of the following methods.

(1) A method which produces cysteamine hydrochloride by preparing cysteamine from ethylene imine and hydrogen sulfide and causing hydrogen chloride to react with cysteamine.

(2) A method which forms cysteamine hydrochloride by adding hydrochloric acid to 2-dimethyl-thiazolidine [JP-B-50-29,444(1975)].

(3) A method which forms cysteamine hydrochloride from monoethanolamine as a starting raw material [JP-A-57-88,171(1982), JP-A-57-144,252(1982), JP-A-55-17,019(1980), JP-A-57-64,684(1982), JP-A-57-53,458(1982), JP-A-57-67,555(1982), and JP-A-57-64,661(1982)].

Heretofore, the cysteamine hydrochloride has been generally handled in a particulate form. The cysteamine hydrochloride itself is stimulative to the human body. Particularly when this compound is inhaled in the form of fine powder, it stimulates the nasal cavity and the pharynx and incites cough and sneeze. When the powder is left adhering to the skin, it causes inflammation. When the cysteamine hydrochloride in a particulate form containing a fine powder in a large proportion is to be handled, therefore, serious attention should be paid to protecting the skin against contact with the compound to the fullest possible extent.

Further, the cysteamine hydrochloride in the powdery form has the disadvantage that it agglomerates into lumps during a protracted storage in a container and defies removal from the container and, even when such lumps are managed to be taken out of the container, must be pulverized prior to use. The lumps of cysteamine hydrochloride have another problem of taking up much time in attaining necessary solution.

The cysteamine hydrochloride in the powdery state, deserves well to be called a highly problematic form of product.

The conventional cysteamine hydrochloride which comes in the powdery form has many problems as described above and entails various inconveniences when it is handled in large amounts normal in commerce.

An object of this invention, therefore, is to provide cysteamine hydrochloride which retains the form imparted as a finished product stably for a long time without either appreciably producing a fine powder or undergoing agglomeration while in storage and a method for the production thereof.

Another object of this invention is to provide granular cysteamine hydrochloride, a method for the production thereof, and an apparatus for practicing the method.

SUMMARY OF THE INVENTION

The objects described above are accomplished by a molded product of cysteamine hydrochloride obtained by preparing powdery cysteamine hydrochloride having a water content of not more than 1% by weight and compression molding the powdery cysteamine hydrochloride under pressure of not less than 50 atmospheres.

These objects are further accomplished by granular cysteamine hydrochloride obtained by cooling and solidifying the resultant molten cysteamine hydrochloride.

These objects are also accomplished by a method for the production of granular cysteamine hydrochloride, which method comprises dropping a molten cysteamine hydrochloride onto a corrosion-proof substrate retained at a temperature of not higher than 65° C. thereby cooling and solidifying the drops of cysteamine hydrochloride.

These objects are further accomplished by a method for the production of granular cysteamine hydrochloride, which method comprises cooling and solidifying a molten cysteamine hydrochloride by the use of a plate type dropping granulating device and which method is characterized by having the cooling substrate of the dropping granulating device cooled with the spray of a polyhydric alcohol-containing solution directed to the lower surface of the substrate.

These objects are also accomplished by a granulating apparatus for cysteamine hydrochloride, which apparatus comprises means for dropping cysteamine hydrochloride, endless conveying means disposed below the dropping means, and cooling means disposed below a cooling substrate of the conveying means, and the cooling means comprising a member for spraying a polyhydric alcohol-containing liquid against the lower surface of the substrate, a member for recovering the polyhydric alcohol-containing liquid, and means for controlling the temperature of the polyhydric alcohol-containing solution.

These objects are also accomplished by a method for the production of granular cysteamine hydrochloride, which method comprises cooling and solidifying the molten cysteamine hydrochloride by the use of a plate type dropping granulating device and which method is characterized by effecting the cooling and solidification of the molten cysteamine hydrochloride by dropping the molten cysteamine hydrochloride onto a metallic substrate formed by coating the surface of a cooling substrate of the plate type dropping granulating device with fluorine resin.

These objects are further accomplished by a granulating apparatus for cysteamine hydrochloride, which apparatus comprises means for dropping cysteamine hydrochloride, endless conveying means disposed below the dropping means, and cooling means disposed below a cooling substrate of the conveying means, and the substrate of the conveying means having the surface thereof coated with fluorine resin.

The molded or granulated product of cysteamine hydrochloride according with the present invention manifests an outstanding effect of avoiding agglomeration while in storage in a container and showing prominent solubility to inorganic acids and organic liquid as compared with the conventional powdery cysteamine hydrochloride. It further has the advantage of not only avoiding the otherwise inevitable possibility of powdery cysteamine hydrochloride stimulating the nasal cavity and the pharynx on inhalation and inducing inflammation of the skin on contact but also preventing the produced granules from substantially absorbing moisture because a polyhydric alcohol-containing solution is used for spray cooling the substrate. Moreover, the substrate coated with fluorine resin enjoys outstanding resistance to corrosion and allows a long service life.

BRIEF DESCRIPTION OF THE DRAWINGS

FIG. 2 is a schematic cross section illustrating a granulating device in one embodiment of this invention, FIG. 3 is a schematic cross section illustrating a dropping device in one embodiment of this invention, and FIG. 4 is a schematic cross section illustrating a dropping device in another embodiment of the present invention.

EXPLANATION OF THE PREFERRED EMBODIMENT

Figure 1:
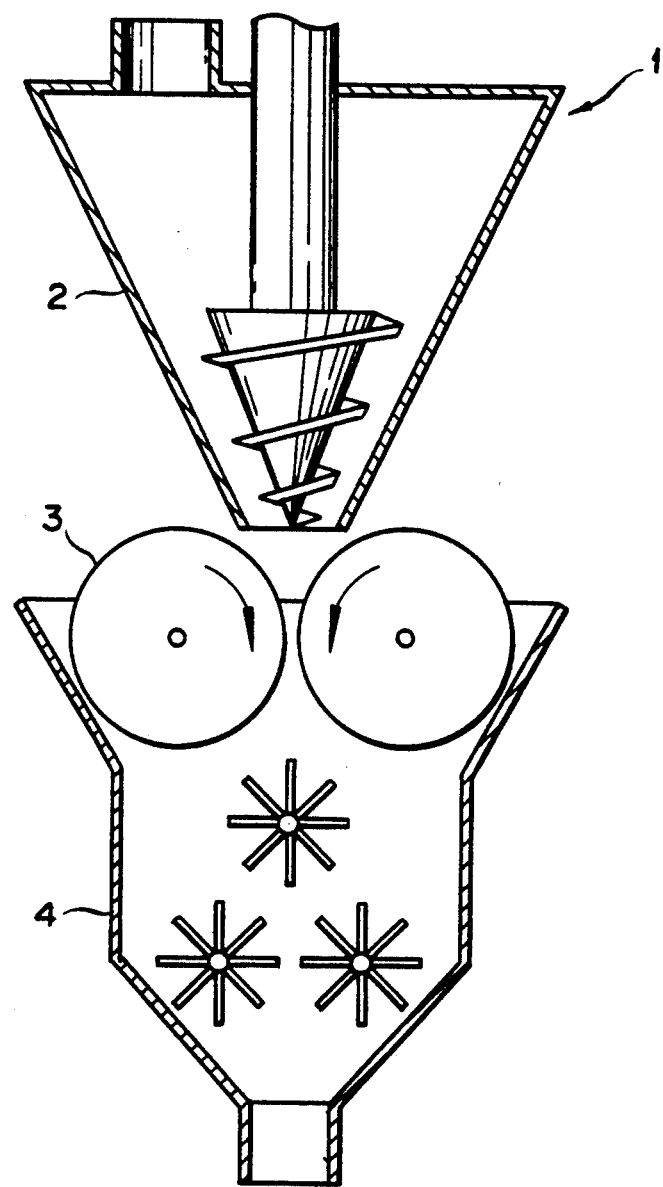
FIG. 1 is a schematic cross section illustrating a molding device in one embodiment of the present invention.

This invention relates to a molded product of cysteamine hydrochloride having an average diameter in the range of 0.01 to 20 mm, preferably 0.1 to 10 mm, characterized by a process of manufacture which comprises preparing powdery cysteamine hydrochloride having a water content of not more than 1% by weight and compression molding the powdery cysteamine hydrochloride under pressure of not less than 50 atmospheres.

This invention also allows the molding of the cysteamine hydrochloride to be effected by the use of a binding agent or a wetting agent.

The cysteamine hydrochloride which can be molded by the method of the present invention assumes a solid state at normal room temperature and possesses a melting point of about 68° C. For the compression of the powdery cysteamine hydrochloride, a pressure generally exceeding 50 atmospheres and preferably falling in the range of 80 to 150 atmosphere is adopted.

The molded cysteamine hydrochloride can be produced, for example, by a method which comprises introducing a white crystalline cysteamine hydrochloride into a holler 2 of a roll type compressing device (a roller compacter) 1 illustrated in FIG. 1, compressing the powder with rollers 3 in the device under pressure of 100 atmospheres thereby producing a molded sheet about 2 mm in thickness, and subsequently treating the sheet with a coarse pulverizing and diameter-adjusting device 4 thereby giving rise to grains of cysteamine hydrochloride having a diameter in the range of 0.01 to 20 mm, preferably 0.1 to 10 mm.

Since the cysteamine hydrochloride is highly hygroscopic and very susceptible of oxidation at an elevated temperature, it is desired to be molded in an atmosphere to nitrogen gas.

The materials which are usable for the part of the compression molding device which is destined to contact the cysteamine hydrochloride powder include such metals as stainless steel, titanium, and Hastelloy TM type alloy ceramics, and such synthetic resins as, for example, Teflon TM type tetrafluoroethylene polyethylene, and polypropylene, for example.

The present invention also relates to granular cysteamine hydrochloride obtained cooling and solidifying the molten cysteamine hydrochlrode. It further relates to a method for the production of granular cysteamine hydrochloride, which method comprises dropping the resultant molten cysteamine hydrochloride onto a corrosion-proof substrate retained at a temperature of not higher than 65° C. thereby cooling and soldfying the drops of cysteamine hydrochloride.

The granular cysteamine hydrochloride according with the present invention possesses an average particle diameter in the range of 0.1 to 20 mm, preferably 1 to 15 mm.

The cysteamine hydrochloride which can be granulated by the method of this invention assumes a solid state at normal room temperature and possesses a melting point of about 68° C. For the melting of the cysteamine hydrochloride, a temperature required to be higher than the melting point and desired to be in the range of 68° C. to 150° C., preferably 70° to 100° C. is adopted. The heating of the cysteamine hydrochloride is carried out in a corrosion-proof container or line provided with heating means such as a jacket, a coil, and/or an electric heater.

Since the cysteamine hydrochloride is highly hygroscopic and very susceptible to oxidation at an elevated temperature, it is preferable to be heated in an atmosphere of nitrogen gas. To be solidified, the molten cysteamine hydrochloride is preferable to be suddenly cooled by being dropped onto a flat and smooth corrosion-proof substrate kept cooled at a temperature not exceeding 65° C., preferably falling in the range of 40° to 10° C. Generally, this cooling is effected below the solidifying point for a period not exceeding 30 minutes. The materials which are usable for the corrosion-proof substrate include such metals as stainless steel, titanium, and Hastelloy TM type alloy, such resins as Teflon TM type tetrafluoroethylene, polypropylene, and polyethylene, and such rubbers as, for example neoprene rubber and Byton rubber.

For the cooling, a method for cooling the surface of the substrate opposite to the surface exposed to the dropping molten cysteamine hydrochloride specifically by circulation of cooling water may be adopted. The method which comprises melting the cysteamine hydrochloride and cooling and solidifying the molten cysteamine hydrochloride is generally carried out under normal pressure. It may be performed, as occasion demands, under a vacuum or under increased pressure. The granulation of the cysteamine hydrochloride is preferable to be attained by cooling and solidifying the molten cysteamine hydrochloride by the use of a plate type dropping granulating device.

The molten cysteamine hydrochloride is supplied to the plate type dropping granulating device. The term "plate type dropping granulating device" as used herein is a general term applied to any of the devices which are adapted to produce granules by dropping a molten substance onto a cooled substrate thereby cooling and solidifying the drops of the molten substance.

In the present invention, the molten cysteamine hydrochloride obtained by heating to a temperature exceeding the melting point is quenched to be solidified and granulated by being dropped onto the corrosion-proof substrate of the dropping granulating device kept cooled below 65° C.

Though the average particle diameter of the granules of cysteamine hydrochloride of this invention is determined by the diameter of the holes for the dropping, the dropping temperature, the temperature of the molten cysteamine hydrochloride, and the speed of movement of the corrosion-proof substrate, it is selected in the range of 0.1 to 20 mm, preferably 1 to 15 mm, depending on the handling as during solidification and the solubility of the product during the course of use. The granules have a hemispherical shape or a semi-ellipsoidal shape.

The belt substrate of the plate type dropping granulating device contemplated by the present invention which is destined to contact the molten cysteamine hydrochloride is flat and smooth and resistant to corrosion. The materials which are usable for the belt substrate include such metals as stainless steel, titanium, and Hastelloy TM type alloy, such resins as Teflon TM type tetrafluoroethyer, polypropylene, and polyethylene, and such rubbers as, for example, Neoprene rubber and Byton rubber.

The substrate of the plate type dropping granulating device of the present invention is cooled generally by a method which comprises supplying cooling water to the substrate and then cooling the used cooling water with a chiller or a cooling tower before it is put to re-use.

For the purpose of preventing the cysteamine hydrochloride from absorbing moisture, it is desired to have the dropping part and the cooling part of the plate type dropping granulating device or the entire device enveloped with a dehumidified atmosphere of an inert gas such as air or nitrogen.

Though the solidifying time is not specifically defined, it is generally within 30 minutes.

Though the method which comprises melting the cysteamine hydrochloride and cooling and solidifying the molten cysteamine hydrochloride is performed generally under normal pressure, it may be carried out, as occasion demands, under a vacuum or under increased pressure.

The present invention can be applied to cysteamine hydrochloride powder produced by various methods and does not discriminate the cysteamine hydrochloride powder on account of the method employed for its production. The cysteamine hydrochloride powder may be produced, for example, by the following method.

There is a method for producing cysteamine hydrochloride by preparing cysteamine by the reaction of hydrogen sulfide with ethylene imine and then causing cysteamine to react with hydrochloric acid. More specifically, hydrogen sulfide is retained in the presence of a solvent under a pressure in the range of 6 to 10 kg/cm$^2$.G, preferably 7 to 10 kg/cm$^2$.G, at a temperature in the range of 0° to 10° C., preferably 0° to 5° C. and ethylene imine is continuously added thereto and allowed to react therewith. Then, the resultant reaction mixture is heated at a temperature 60° to 70° C. and stripped of hydrogen sulfide. The residue and hydrochloric acid added thereto are cooled to a temperature below 5° C., preferably in the range of 0° to 5° C., to induce precipitation of crystals. The crystals are separated by filtration and dried in an atmosphere of nitrogen gas.

The solvents which are usable in this invention include alcohols such as methanol, ethanol, and propy alcohol, ketones such as acetone, and water, for example. Among other solvents mentioned above, methanol or ethanol proves to be particularly desirable.

There is another method for producing cysteamine hydrochloride by causing the sulfuric ester of 2-aminoethanol to react with carbon disulfide in the presence of an alkali hydroxide and then hydrolyzing 2-mercapothiazoline, the reaction product, with hydrochloric acid. More specifically, in an aqueous solution containing an alkali hydroxide in a concentration in the range of 20 to 40% by weight, the sulfuric ester of 2-aminoethanol is caused to react with carbon disulfide at a temperature in the range of 20° to 90° C., preferably 30° to 60° C., for a period in the range of 1 to 15 hours, preferably 4 to 6 hours, to form 2-mercaptothiazoline. This 2-mercaptothiazoline is hydrolyzed with hydrochloric acid to give birth to cysteamine hydrochloride.

There is yet another method for producing cysteamine hydrochloride by causing 2-aminoethyl sulfuric ester to react with sodium thiosulfate in the presence of an alkali hydroxide and then hydrolyzing S-(2-aminoethyl)thiosulfate, the reaction product, with hydrochloric acid. To be more specific, the 2-aminoethanol sulfuric ester is caused to react with sodium thiosulfate in an aqueous solution containing an alkali hydroxide in a concentration in the range of 20 to 45% by weight at a temperature in the range of at least 20° C., preferably at least 50° C., for a period in the range of 1 to 50 hours, preferably 2 to 40 hours so form S-(2-aminoethyl)thiosulfate. This S-(2-aminoethyl)thiosulfate is hydrolyzed with hydrochloric acid to give birth to the cysteamine hydrochloride.

There is still another method for producing cysteamine hydrochloride by causing 2-chloroethylamine hydrochloride to react with 2-mercaptothiazolidine in the presence of a solvent and then hydrolyzing 2-(2'-aminoethylthio)-thiazolidine hydrochloride, the reaction product, with hydrochloric acid. To be more specific, 2-chloroethylamine hydrochloride is dissolved in a concentration in the range of 30 to 70% by weight in a solvent. The resultant solution is caused to react with 2-mercaptothiazolidine at a temperature in the range of at least 20° C., preferably at least 50° C., for a period in the range of 1 to 50 hours, preferably 2 to 40 hours, to form 2-(2'-aminoethylthio)thiazolidine hydrochloride. Then, this reaction product is hydrolyzed with hydrochloric acid. The solvents which are usable in this reaction include, for example, water, methanol, ethanol, isopropanol, etc.

There is further a method for producing cysteamine hydrochloride by causing a 2-dialkylthiazoline to react with water and a halogenated hydroacid in the presence of a solvent. To be more specific, the 2-dialkylthiazolidine is hydrolyzed with the halogenated hydroacid in the presence of a solvent, with the pH value adjusted in the range of 1.5 to 5.0, preferably 2 to 4, and the temperature elevated to a level in the range of 40° to 180° C., preferably 100 to 150° C. Then, the hydrolyzate is deprived of the solvent under a vacuum.

The solvents which are usable in this invention include such polar solvents as water and alcohols, for example. Among other solvents mentioned above, water proves to be particularly desirable. The 2-dialkylthiazolidines which are usable in this invention include, for example 2-dimethylthiazolidine and 2-dimethylethyl thiazolidine. Particularly, 2-dimethyl thiazolidine proves to be desirable. The halogenated hydroacids which are usable in the present invention include, for example, hydrochloric acid and hydrobromic acid. Particularly, hydrochloric acid proves to be desirable. The cysteamine hydrochlorides which are obtainable in the present invention include, for example aminoethane thiol salt and β-aminoethylmercaptan salt. Particularly, cysteamine hydrochloride (aminoethane thiol hydrochloride) is obtained desirably.

According to the present invention, the cysteamine hydrochloride can also been obtained by adding hydrochloric acid in an amount of not less than equivalent amount to 2-dialkyl thiazolines represented by the formula I

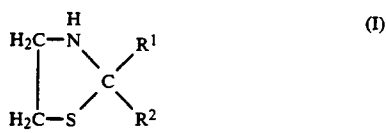

wherein $R^1$ and $R^2$ are independently at least one alkyl group selected from an alkyl group having 1 to 2 carbon atoms, in the presence of water under removing a by-produced dialkyl ketones continuously out of the reaction system, elevating a temperature to 130° to 160° C. to complete the reaction, and removing water in vacuo under maintaining 68° to 160° C.

This invention relates to a method for the production of granular cysteamine hydrochloride, which comprises granulating cysteamine hydrochloride by cooling and solidifying the molten cysteamine hydrochloride by the use of a plate type dropping granulating device while having the cooling substrate of the plate type dropping granulating device kept cooled by spraying a polyhydric alcohol-containing solution on the lower surface of the substrate. Further, this invention relates to a granulating apparatus for cysteamine hydrochloride, which comprises means for dropping molten cysteamine hydrochloride, means for endless conveyance dispoded below the dropping means, and cooling means disposed below a cooling substrate of the conveyance means, the cooling means comprising a member for sparying a polyhydric alcohol-containing solution on the lower surface of the substrate, a member for recovering the polyhydric alcohol-containing solution, and means for controlling the temperature of the polyhydric alcohol-containing solution.

Now, the preferred embodiment of this invention will be described below with reference to the accompanying drawings.

FIG. 2 is a schematic cross section illustrating an apparatus for practicing the method of the present invention. Inside a granular granulating chamber 12 installed in a building 11, a conveying device 13 such as, for example, a belt conveyor comprising rolls 14, 15 and an endless belt 16. Below the endless belt 16 is disposed a coolant spraying device 17. Below this spraying device 17 is disposed a coolant recovering device 18. To this spraying device 17, a conduit 20 extended from a cooling device 19 is connected through the medium of a pump 21. To the recovering device 18, a conduit 22 extended from a cooling device 19 is connected. To the cooling device 19, a coolant such as brine is supplied via a conduit 23 to keep the cooling device 19 at a prescribed temperature.

A dropping device 24 for molten cysteamine hydrochloride is disposed above the conveying device 13 and in the nearmost part relative to the direction of motion of the conveyor. To this dropping device 24 is connected a conduit 25 extended from a melting device (not shown) for cysteamine hydrochloride.

A hopper 26 is connected to the lower part of the granulating chamber 12 in the downstream end part relative to the direction of motion of the conveyor. Conduits 27, 28 connected to a dehumidifying device (not shown) are extended through a pump 29 and connected to the interior of the building 11 and the hopper 26. To the opposite side of the building 11, an exhaust gas conduit 30 is connected.

Now, the method for granulating cysteamine hydrochloride by the use of the apparatus constructed as described above will be explained below. First, the cysteamine hydrochloride melted by the melting device (not shown) or melted cysteamine hydrochloride obtained from a reactor (not shown) in a molten state is supplied to the dropping device 24 through a conduit 25 which is kept warm as occasion demands and caused to fall in drops 31 therefrom onto the belt conveyor 16. The drops 31 deposited on the belt conveyor 16 in motion are cooled and solidified into granules as the coolant spraying device 17 sprays a polyhydric alcohol-containing liquid on the lower surface of the belt conveyor 16. The sprayed polyhydric alcohol-containing liquid, on fulfilling the role of cooling the belt conveyor 16, is recovered by the recovering device 18. Though this recovering device 18 may assume a varying form, it is generally used in the form of a tray. A recovered polyhydric alcohol-containing liquid 32 is forwarded through the conduit 22 to the cooling device 19, cooled therein to a prescribed temperature, and forwarded through the conduit 20 to the coolant spraying device 17 by means of the pump 21.

The granules formed as described above are scraped by a scraper 42 and discharged via the hopper 26. Dry air, when necessary, is introduced through the conduits 27, 28 into the building 11 and the hopper 26 and discharged through the exhaust gas conduit 30, so as to keep the interior of the building 11 and the interior of the hopper 26 in a dry state.

The polyhydric alcohol-containing liquids which are usable in the present invention include ethylene glycol, diethylene glycol, triethylene glycol, tetraethylene glycol, propylene glycol, dipropylene glycol, tripropylene glycol, glycerin, butane diol, neopentyl glycol, and pentaerythritol, for example, which may be used singly, as suitably combined, or as dissolved in water. Among other polyhydric alcohol-containing liquids mentioned above, ethylene glycol, diethylene glycol, and propylene glycol prove to be preferable. Ethylene glycol proves to be most preferable.

The polyhydric alcohol-containing liquid which is supplied to the coolant spraying device absorbs the moisture from within the gas filling the granulating device and consequently serves the purpose of keeping the interior of the granulating device in a dry state. When the polyhydric alcohol-containing liquid is diluted with the absorbed moisture to below a prescribed concentration, is discharged through an outlet 33. A new supply of the polyhydric alcohol-containing liquid is introduced through an inlet 34 by way of replenishment.

The dropping device 24 may be in a varying form. For example, as illustrated in FIG. 3, it comprises a stationary inner tube 34, a porous outer tube 35 disposed coaxially with and rotatably around the inner tube 34, a liquid reservoir 36 excavated near the axis of the inner tube 34 and adapted to receive molten cysteamine hydrochloride supplied through the conduit 25, and a slit 37 formed in the lower part of the inner tube 34 and adapted to drop this molten cysteamine hydrochloride onto the conveyor belt 16. In this case, the molten cysteamine hydrochloride is allowed to fall in drops when the holes in the outer tube 25 coincide with the slit and prevented from falling when the closed wall part of the outer tube 25 is passing the slit.

It is otherwise permissable, as illustrated in FIG. 4, to form a hollow part having a piston 39 inserted through a dropping member proper 38 and allow the conduit 25 to communicate with the hollow part, so that the molten cysteamine hydrochloride will be allowed to fall through lower holes 41 in drops onto the belt conveyor 16 in consequence of the reciprocation of the piston 39.

In this case, the endless belt 16 is made of a metal such as stainless steel, aluminum, or copper and is desired to have the surface thereof coated with fluorine resin. The fluorine resin coating has a thickness generally in the range of 0.001 to 1 mm, preferably 0.001 to 0.5 mm. If this thickness is less than 0.001 mm, the coating is deficient in durability. Conversely, if this thickness exceeds 1 mm, the coating is deficient in thermoconductivity and expensive. The coating may be carried out, for example, by a normal temperature dry spray method and fluorine resin sticking method. The fluorine resins which are usable for the coating include polytetrafluoroethylene, tetrafluoroethylene-hexafluoropropylene copolymer, polyvinylidene fluoride, polyvinyl fluoride, and tetrafluoroethylene-perfluorovinyl ether copolymer, for example. Among the fluorine resins mentioned above, polytetrafluoroethylene proves to be particularly desirable.

The coating of the fluorine resin mentioned above can be easily formed by impregnating cloth of glass fibers with the fluorine resin, attaching the impregnated glass-fiber cloth fast to an adhesive sheet, and joining the resultant composite to the endless belt of metal through the medium of the adhesive sheet.

Now, the present invention will be described more specifically below with reference to working examples and controls.

METHOD OF TESTING SOLUBILITY

In four widemouthed sample vials of glass having an inner volume of 200 cc, 30 g each of a given granular cysteamine hydrochloride was placed and, with the entrapped air displaced with nitrogen, was left standing in a hermetically sealed condition at 20° C. for 0 days, 7 days, 14 days, and 30 days before the vials were opened.

(1) In a beaker having an inner volume of 100 ml and held under an atmosphere of nitrogen gas, 40 ml of an aqueous 35 wt % hydrochloric acid solution and 10 g of the granular cysteamine hydrochloride added thereto were mixed with a stirrer at a rotational rate of 200 rpm at 25° C. to determine the time required for the granules to dissolve in the aqeous solution.

(2) In a beaker having an inner volume of 100 ml and held under an atmosphere of nitrogen gas, 25 ml of ethanol and 8 g of the granular cysteamine hydrochloride added thereto were mixed with a stirrer at a rotational rate of 200 rpm at 25° C. to determine the time required for the granules to dissolve in the ethanol.

METHOD FOR TESTING AGGLOMERATION

In four widemouthed sample vials of glass having an inner volume of 200 cc, 30 g each of a given granular cysteamine hydrochloride was placed and, with the entrapped air displaced with nitrogen, was left standing in a hermetically sealed condition at 20° C. for 0 day, 7 days, 14 days, and 30 days. Thereafter, the vials were turned upside down and their contents were visually examined as to the condition of motion of particles therein.

EXAMPLE 1

In an autoclave having an inner volume of 1 m$^3$, 200 liters of methanol was placed and the air entrapped therein was displaced with nitrogen gas. When 136 g (4 kilomols) of hydrogen sulfide was introduced into the system while in a stirred state with the temperature thereof adjusted in the range of 0° to 5° C., the pressure of the system reached 8.6 kg/cm$^2$. With the temperature of the system maintained in the range of 0° to 5° C., a solution of 86 kg (2 kilomols) of ethylene imine in 100 liters of methanol was continuously added for reaction to the system while in a stirred state over a period of 2 hours. After completion of the reaction, the pressure of the system was 3.6 kg/cm$^2$ G. The resultant reaction mixture was heated as sealed under an atmosphere of nitrogen gas until a small amount of the methanol was distilled out, to effect expulsion of hydrogen sulfide. It was further cooled to 5° C. to induce precipitation of crystals. The crystals were separated by filtration and then dried in an atmosphere of nitrogen gas, to afford white crystalline cysteamine.

The cysteamine thus obtained was transferred into a reaction kettle lined with glass, dissolved in 600 liters of isopropyl alcohol, and then blown with 73 kg of hydrogen chloride gas, to give rise to a cysteamine hydrochloride solution. This solution was cooled to 5° C. to induce precipitation of crystals. The crystals were separated by filtration and dried in an atmosphere of nitrogen gas, to obtain white crystalline cysteamine hydrochloride.

The white crystalline cysteamine hydrochloride powder thus obtained was placed in the hopper 2 of the roll type compressing device (roller compacter) 1 constructed as illustrated in FIG. 1 and compressed with rollers under a roll pressure of 100 atmospheres to produce a sheet. Then, the sheet was treated with the coarse pulverizing and diameter-adjusting device 4. The molded product of cysteamine hydrochloride consequently obtained had particle diameters in the range of 0.5 to 5 mm.

The molded cysteamine hydrochloride was left standing at 30° C. for a varying length of time, i.e. 0 to 30 days, and then tested for solubility in an aqueous 35 wt % hydrochloric acid solution and ethanol and for susceptibility to all agglomeration.

The results of the test for solubility are shown in Table 1 and those of the test for agglomeration in Table 2.

TABLE 1

| Number of days of standing | Time for solution (min) in aqueous 35 wt % HCl soln. | Time for solution (min) in ethanol |
| --- | --- | --- |
| 0 | 2.2 | 28 |
| 7 | 2.1 | 28 |
| 14 | 2.1 | 28 |

TABLE 1-continued

| Number of days of standing | Time for solution (min) in aqueous 35 wt % HCl soln. | Time for solution (min) in ethanol |
|---|---|---|
| 30 | 2.2 | 28 |

TABLE 2

| Number of days of standing | Condition of motion |
|---|---|
| 0 | Absence of cohesion between particles |
| 7 | Absence of cohesion between particles |
| 14 | Absence of cohesion between particles |
| 30 | Absence of cohesion between particles |

CONTROL 1

In vials having the entrapped air displaced with nitrogen gas, samples of the same white crystalline cysteamine hydrochloride powder as obtained in Example 1 were left standing at 30° C. for varying lengths of time, i.e. 0 to 30 days. After the standing, the samples in their undissolved form were tested for solubility in an aqueous 35 wt % hydrochloric acid solution and ethanol and for susceptibility to agglomeration.

The results of the test for solubility are shown in Table 3 and those of the test for agglomeration in Table 4.

TABLE 3

| Number of days of standing | Time for solution (min) in aqueous 35 wt % HCl soln. | Time for solution (min) in ethanol |
|---|---|---|
| 0 | 2 | 25 |
| 7 | 23 | 68 |
| 14 | 28 | 75 |
| 30 | 30 | 82 |

TABLE 4

| Number of days of standing | Condition of motion |
|---|---|
| 0 | Absence of cohesion between particles |
| 7 | Agglomerated |
| 14 | Agglomerated |
| 30 | Agglomerated |

EXAMPLE 2

The same white crystalline cysteamine hydrochloride powder as obtained in Example 1 was dissolved by heating to 80° C., aspirated in a Pasteur Pipet 2 mm in mouth diameter, and dropped onto a plate of polytetrafluoroethylene (marketed under trademark designation of "Teflon") having the opposite side kept at 30° C. by cooling with water. The white solid heaps of cysteamine hydrochloride deposited consequently on the Teflon plate were hemispheres 3 to 5 mm in diameter and 2 to 3 mm in height.

The granular cysteamine hydrochloride thus obtained was left standing at 30° C. for varying lengths of time, i.e. 0 to 30 days, and then tested for solubility in an aqueous 35 wt % hydrochloric acid solution and ethanol and for susceptibility to agglomeration.

The results of the test for solubility are shown in Table 5 and those of the test for agglomeration in Table 6.

TABLE 5

| Number of days of standing | Time for solution (min) in aqueous 35 wt % HCl soln. | Time for solution (min) in ethanol |
|---|---|---|
| 0 | 2.5 | 32 |
| 7 | 2.4 | 32 |
| 14 | 2.5 | 32 |
| 30 | 2.5 | 32 |

TABLE 6

| Number of days of standing | Condition of motion |
|---|---|
| 0 | Absence of cohesion between particles |
| 7 | Absence of cohesion between particles |
| 14 | Absence of cohesion between particles |
| 30 | Absence of cohesion between particles |

EXAMPLE 3

White solid cysteamine hydrochloride hemispheres 10 to 15 mm in diameter and 5 to 6 mm in height obtained as deposited on a polytetrafluoroethylene by following the procedure of Example 2 were tested for solubility in an aqueous 35 wt % hydrochloric acid solution and for susceptibility to agglomeration in the same manner as in Example 1.

The results of the test for solubility are shown in Table 7 and those of the test for agglomeration in Table 8.

TABLE 7

| Number of days of standing | Time for solution (min) in aqueous 35 wt % HCl soln. |
|---|---|
| 0 | 5.4 |
| 7 | 5.5 |
| 14 | 5.4 |
| 30 | 5.4 |

TABLE 8

| Number of days of standing | Condition of motion |
|---|---|
| 0 | Absence of cohesion between particles |
| 7 | Absence of cohesion between particles |
| 14 | Absence of cohesion between particles |
| 30 | Absence of cohesion between particles |

EXAMPLE 4

In an autoclave having an inner volume of 1 m$^2$, 200 liters of methanol was placed and the air entrapped therein was displaced with nitrogen gas. When 136 kg (4 kilomols) of hydrogen sulfide was introduced into this system while in a stirred state, with the temperature of the system adjusted in the range of 0° to 5° C., the pressure of the system reached 8.6 kg/cm2 G. With the temperature of this system kept in the range of 0° to 5° C., a solution of 86 kg (2 kilomols) of ethylene imine in 100 liters of methanol was continuously added for reaction to the system while in a stirred state over a period of 2 hours. After completion of the reaction, the pressure of the system was 3.6 kg/cm$^2$ G.

The resultant reaction mixture was heated as sealed in an atmosphere of nitrogen gas until a small amount of the methanol was distilled out, to effect expulsion of the hydrogen sulfide. The reaction mixture was further cooled to 5° C. to induce precipitation of crystals. The crystals were separated by filtration and then dried in an atmosphere of nitrogen gas, to afford white crystalline cysteamine.

The cysteamine thus obtained was transferred into a reaction vessel lined with glass, dissolved in 600 liters of isopropyl alcohol, and then blown with 73 kg of hydrogen chloride gas, to give rise to cysteamine hydrochloride solution. This solution was cooled to 5° C. to induce precipitation of crystals. The crystals were separated by filtration and then dried in an atmosphere of nitrogen gas, to produce white crystalline cysteamine hydrochloride.

The white crystalline cysteamine hydrochloride powder thus obtained was melted by heating to about 72° C., supplied to a plate type dropping granulating device, and dropped onto a sheet of polytetrafluoroethylene applied fast to a flat smooth platelike belt of steel having the opposite side thereof cooled with water to 30° C. The white solid heaps of cysteamine hydrochloride consequently deposited on the sheet were hemispheres 3 to 5 mm in diameter and 1 to 3 mm in height.

The granules of cysteamine hydrochloride thus obtained were left standing at 30° C. for varying lengths of time, i.e. 0 to 30 days, and then tested for solubility in an aqueous 35 wt % hydrochloric acid solution and ethanol and for susceptibility to agglomeration.

The results of the test for solubility are shown in Table 9 and those of the test for agglomeration in Table 10.

TABLE 9

| Number of days of standing | Time for solution (min) in aqueous 35 wt % HCl soln. | Time for solution (min) in ethanol |
|---|---|---|
| 0 | 1.9 | 25 |
| 7 | 1.8 | 25 |
| 14 | 1.9 | 25 |
| 30 | 1.9 | 25 |

TABLE 10

| Number of days of standing | Condition of motion |
|---|---|
| 0 | Absence of cohesion between particles |
| 7 | Absence of cohesion between particles |
| 14 | Absence of cohesion between particles |
| 30 | Absence of cohesion between particles |

EXAMPLE 5

White solid cysteamine hydrochloride hemispheres 10 to 15 mm in diameter and 5 to 6 mm in height obtained by following the procedure of Example 4 were tested for solubility in an aqueous 35 wt % hydrochloric acid solution and for susceptibility to agglomeration.

The results of the test for solubility are shown in Table 11 and those of the test for agglomeration in Table 12.

TABLE 11

| Number of days of standing | Time for solution (min) in aqueous 35 wt % HCl soln. |
|---|---|
| 0 | 4.2 |
| 7 | 4.2 |
| 14 | 4.2 |
| 30 | 4.2 |

TABLE 12

| Number of days of standing | Condition of motion |
|---|---|
| 0 | Absence of cohesion between particles |
| 7 | Absence of cohesion between particles |
| 14 | Absence of cohesion between particles |
| 30 | Absence of cohesion between particles |

EXAMPLE 6

The same cysteamine as obtained in Example 1 was transferred into a separable flask of glass, dissolved in 600 ml of isopropyl alcohol, and blown with 73 g of hydrogen chloride gas, to obtain cysteamine hydrochloride solution. This solution was cooled to 5° C. to induce precipitation of crystals. The crystals were separated by filtration and dried in an atmosphere of nitrogen and heated to 80° C. to be thoroughly dissolved. The solution was aspired with a Pasteur pipet 2 mm in mouth diameter and dropped onto a plate of tetrafluoroethylene having the opposite side thereof cooled with water to 30° C. The white solid cysteamine hydrochloride heaps deposited on the plate were hemispheres 3 to 5 mm in diameter and 2 to 3 mm in height.

The cysteamine hydrochloride hemispheres thus obtained were left standing at 30° C. for varying lengths of time, i.e. 0 to 30 days, and then tested for solubility in an aqueous 35 wt % hydrochloric acid solution and ethanol and for susceptibility to agglomeration.

The results of the test for solubility are shown in Table 13 and those of the test for agglomeration in Table 14.

TABLE 13

| Number of days of standing | Time for solution (min) in aqueous 35 wt % HCl soln. | Time for solution (min) in ethanol |
|---|---|---|
| 0 | 2.6 | 32 |
| 7 | 2.4 | 33 |
| 14 | 2.6 | 34 |
| 30 | 2.5 | 33 |

TABLE 14

| Number of days of standing | Condition of motion |
|---|---|
| 0 | Absence of cohesion between particles |
| 7 | Absence of cohesion between particles |
| 14 | Absence of cohesion between particles |
| 30 | Absence of cohesion between particles |

EXAMPLE 7

White solid cysteamine hydrochloride hemispheres 10 to 15 mm in diameter and 5 to 6 mm in height obtained by following the procedure of Example 6 were tested for solubility in an aqueous 35 wt % hydrochloric acid solution and for susceptibility to agglomeration in the same manner as in Example 1.

The results of the test for solubility are shown in Table 15 and those of the test for agglomeration in Table 16.

TABLE 15

| Number of days of standing | Time for solution (min) in aqueous 35 wt % HCl soln. |
|---|---|
| 0 | 5.4 |
| 7 | 5.6 |
| 14 | 5.4 |

TABLE 15-continued

| Number of days of standing | Time for solution (min) in aqueous 35 wt % HCl soln. |
|---|---|
| 30 | 5.5 |

TABLE 16

| Number of days of standing | Condition of motion |
|---|---|
| 0 | Absence of cohesion between particles |
| 7 | Absence of cohesion between particles |
| 14 | Absence of cohesion between particles |
| 30 | Absence of cohesion between particles |

EXAMPLE 8

In a reaction vessel provided with a stirrer, a temperature-regulating device, a refluxing device, and a dropping funnel, 0.1 mol of sulfuric ester of 2-aminoethanol was dissolved at room temperature in an aqueous 20 wt % sodium hydroxide solution containing 0.2 mol of sodium hydroxide. The solution and 0.2 mol of carbon disulfide added thereto were thoroughly stirred, gradually heated to the neighborhood of the boiling point of carbon disulfide, and left reacting at that temperature for 2 hours. Then, the resultant reaction mixture and an aqeous 20 wt % sodium hydroxide solution added thereto in an amount of 0.2 mol as sodium hydroxide were left reacting further for 3 hours. The reaction mixture, during the secondary reaction, allowed occurrence of reflux because of a slight residue of carbon disulfide. The residue was completely consumed, however, in the latter half phase of the reaction. Finally, the temperature was raised to 60° C. to terminate the reaction. Then, the reaction mixture was hot filtered at a temperature above 40° C. The crude crystals consequently obtained was thoroughly washed with cold water, to obtain white 2-mercaptothiazoline crystals. The purity of the product was 99.4% and the yield of the product based on the supplied 2-aminoethanol sulfiric ester was 93.3%.

In a glass autoclave having an inner volume of 1 liter, 119.3 g (1.0 mol) of 2-mercaptothiazoline and 650 cc (4.23 mols) of 21 wet 21 wt % hydrochloric acid were refluxed at 102° C. under a pressure of 2.5 kg/cm2 G for 45 hours. After the reaction was stopped, the reaction mixture was gradually reverted to normal pressure and treated with a rotary evaporator for 1 hour and heated under a vacuum at 80° C. for 1 hour to effect thorough expulsion of hydrogen chloride and water and concentration to dryness.

Subsequently, the recrystallized concentrate and 60 cc of methanol (purity 99.9%) added thereto as a solvent were heated and stirred for thorough solution. The resultant solution was amply stirred and cooled to 5° C. to induce precipitation of crystals. The crystals were separated by suction filtration. The produced crystals of cysteamine hydrochloride were dried under a vacuum at 40° C. for 2 hours and then thoroughly dissolved by heating to a temperature above 80° C. The solution was aspired with a Pasteur pipet 2 mm in mouth diameter and dropped onto a tetrafluoroethylene plate having the opposite side thereof cooled with water to 30° C. The white solid cysteamine hydrochloride heaps consequently deposited on the plate were hemispheres 3 to 5 mm in diameter and 2 to 3 mm in height.

The hemispheres of cysteamine hydrochloride thus obtained were left standing at 30° C. for varying lengths of time, i.e. 0 to 30 days, and then tested for solubility in an aqueous 35 wt % hydrochloric acid solution and ethanol and for susceptibility to agglomeration.

The results of the test for solubility are shown in Table 17 and those of the test for agglomeration in Table 18.

TABLE 17

| Number of days of standing | Time for solution (min) in aqueous 35 wt % HCl soln. | Time for solution (min) in ethanol |
|---|---|---|
| 0 | 2.3 | 31 |
| 7 | 2.3 | 31 |
| 14 | 2.4 | 30 |
| 30 | 2.3 | 32 |

TABLE 18

| Number of days of standing | Condition of motion |
|---|---|
| 0 | Absence of cohesion between particles |
| 7 | Absence of cohesion between particles |
| 14 | Absence of cohesion between particles |
| 30 | Absence of cohesion between particles |

CONTROL 2

In vials having the trapped air therein displaced with nitrogen, samples of the same which crystalline cysteamine hydrochloride powder as obtained in Example 8 were left standing at 30° C. for varying lengths of time, i.e. 0 to 30 days, and were tested in their undissolved state to solubility in an aqueous 35 wt % hydrochloric acid solution and ethanol and for susceptibility to agglomeration.

The results of the test for solubility are shown in Table 19 and those of the test for agglomeration in Table 20.

TABLE 19

| Number of days of standing | Time for solution (min) in aqueous 35 wt % HCl soln. | Time for solution (min) in ethanol |
|---|---|---|
| 0 | 3 | 27 |
| 7 | 25 | 70 |
| 14 | 30 | 75 |
| 30 | 33 | 85 |

TABLE 20

| Number of days of standing | Condition of motion |
|---|---|
| 0 | Absence of cohesion between particles |
| 7 | Agglomerated |
| 14 | Agglomerated |
| 30 | Agglomerated |

EXAMPLE 9

In a four-neck flask having an inner volume of 100 ml and provided with a stirrer, a thermometer, a reflux condenser, and a nitrogen gas inlet, 14.1 g (0.1 mol) of 2-aminoethyl sulfuric ester, 16.3 g (0.1 mol) of sodium thiosulfate, and 30 g of water were placed and the resultant reaction solution was adjusted to a pH of about 9.0 by addition of sodium hydroxide. The reaction solution was heated and stirred at a refluxing temperature for 20 hours as gently swept with nitrogen gas. After completion of the reaction, the reaction solution assumed a pH of about 6.5. This reaction solution was filtered to remove the greater part of sodium sulfate. The filtrate was concentrated under a vacuum to dryness. On analysis with an IR and a H-NMR, the product was identified to be practically pure (100%) S-(2-aminoethyl)thiosulfate.

In a four-neck flask provided with a stirrer, a thermometer, a reflux condenser, and a dropping funnel, 50 g of 20 wt % sulfuric acid was placed. In the dropping funnel, 78.5 g of an aqueous 40 wt % S-(2-aminoethyl)-thiosulfate solution was placed. The flask was heated in an oil bath to keep the inner temperature thereof in the range of 100° to 105° C. and the aqueous thiosulfate solution was added dropwise to the sulfuric acid from the dropping funnel over a period of about 2 hours. The resultant reaction solution was cooled to room temperature, diluted with water, and treated with an anion-exchange resin, Amberlite IRA 400. Then, hydrochloric acid was added to the reaction solution until the pH value reached 4. The resultant solution was concentrated to dryness under a vacuum and subsequently dried under a vacuum, to obtain 25.3 g of powder. When this powder was assayed by iodometry for determination of the SH group, it was found to be cysteamine hydrochloride having a purity of 96.3% (yield 94.2). When this powder was assayed by the thin-layer chromatography, the presence of a very feeble spot of bis(2-aminoethyl)disulfide was recognized. This cysteamine hydrochloride powder was recrystallized from isopropanol, dried under a vacuum, and then dissolved thoroughly by heating to a temperature above 80° C. The resultant solution was aspired with a Pasteur pipet 2 mm in mouth diameter and dropped onto a tetrafluoroethylene plate having the opposite side thereof cooled with water to 30° C. The white solid cysteamine hydrochloride heaps consequently deposited on the plate were hemispheres 3 to 5 mm in diameter and 2 to 3 mm in height.

Samples of the granules of the cysteamine hydrochloride thus obtained were left standing at 30° C. for a varying lengths of time, i.e. 0 to 30 days, and then tested for solubility in an aqueous 35 wt % hydrochloric acid solution and ethanol and for susceptibility to agglomeration.

The results of the test for solubility are shown in Table 21 and those of the test for agglomeration in Table 22.

TABLE 21

| Number of days of standing | Time for solution (min) in aqueous 35 wt % HCl soln. | Time for solution (min) in ethanol |
|---|---|---|
| 0 | 2.8 | 34 |
| 7 | 2.8 | 34 |
| 14 | 2.7 | 34 |
| 30 | 2.7 | 34 |

TABLE 22

| Number of days of standing | Condition of motion |
|---|---|
| 0 | Absence of cohesion between particles |
| 7 | Absence of cohesion between particles |
| 14 | Absence of cohesion between particles |
| 30 | Absence of cohesion between particles |

CONTROL 3

In vials having the entrapped air displaced with nitrogen gas, samples of the same white crystalline cysteamine hydrochloride powder as obtained in Example 9 were left standing at 30° C. for varying lengths of time, i.e. 0 to 30 days, and then tested for solubility in an aqueous 35 wt % hydrochloric acid solution and ethanol and for susceptibility to agglomeration.

The results of the test for solubility are shown in Table 23 and those of the test for agglomeration in Table 24.

TABLE 23

| Number of days of standing | Time for solution (min) in aqueous 35 wt % HCl soln. | Time for solution (min) in ethanol |
|---|---|---|
| 0 | 3 | 24 |
| 7 | 26 | 66 |
| 14 | 28 | 75 |
| 30 | 35 | 81 |

TABLE 24

| Number of days of standing | Condition of motion |
|---|---|
| 0 | Absence of cohesion between particles |
| 7 | Agglomerated |
| 14 | Agglomerated |
| 30 | Agglomerated |

EXAMPLE 10

In 100 ml of benzene, 0.1 mol of 2-chloroethylamine hydrochloride and 0.1 mol of 2-mercaptothiazoline were dispersed, gradually heated to 80° C., and stirred for reaction at this temperature for 30 minutes. After completion of the reaction, the reaction mixture was filtered to obtain white 2-(2-aminoethylthio)-thiazoline dihydrochloride powder in a yield of 99.7%. In 100 ml of 36 wt % hydrochloric acid, 23.5 g (0.1 mol) of 2-(2-aminoethylthio)-thiazoline dihydrochloride was dissolved. The resultant solution was refluxed for 30 hours, to obtain cysteamine hydrochloride. Then, the cysteamine hydrochloride was concentrated to dryness under a vacuum and then thoroughly dissolved by heating to a temperature above 80° C. The solution was aspired with a Pasteur pipet 2 mm in mouth diameter and dropped onto a tetrafluoroethylene plate having the opposite side thereof cooled with water to 30° C. The white solid cysteamine hydrochloride heaps consequently deposited on the plate were hemispheres 3 to 5 mm in diameter and 2 to 3 mm in height.

The cysteamine hydrochloride hemispheres thus obtained were left standing at 30° C. for a varying lengths of time, i.e. 0 to 30 days, and then tested for solubility in an aqueous 35 wt % hydrochloric acid solution and ethanol and for susceptibility to agglomeration.

The results of the test for solubility are shown in Table 25 and those of the test for agglomeration in Table 26.

TABLE 25

| Number of days of standing | Time for solution (min) in aqueous 35 wt % HCl soln. | Time for solution (min) in ethanol |
|---|---|---|
| 0 | 2.7 | 34 |
| 7 | 2.5 | 32 |
| 14 | 2.6 | 33 |
| 30 | 2.5 | 33 |

TABLE 26

| Number of days of standing | Condition of motion |
|---|---|
| 0 | Absence of cohesion between particles |
| 7 | Absence of cohesion between particles |
| 14 | Absence of cohesion between particles |
| 30 | Absence of cohesion between particles |

CONTROL 4

In vials having the entrapped air therein displaced with nitrogen gas, samples of the same white crystalline cysteamine hydrochloride powder as obtained in Example 10 were left standing at 30° C. for varying lengths of time, i.e. 0 to 30 days, and then, in their undissolved state, tested for solubility in an aqueous 35 wt % hydrochloric acid solution and ethanol and for susceptibility to agglomeration.

The results of the test for solubility are shown in Table 27 and those of the test for agglomeration in Table 28.

TABLE 27

| Number of days of standing | Time for solution (min) in aqueous 35 wt % HCl soln. | Time for solution (min) in ethanol |
|---|---|---|
| 0 | 2 | 25 |
| 7 | 24 | 70 |
| 14 | 25 | 70 |
| 30 | 30 | 83 |

TABLE 28

| Number of days of standing | Condition of motion |
|---|---|
| 0 | Absence of cohesion between particles |
| 7 | Agglomerated |
| 14 | Agglomerated |
| 30 | Agglomerated |

EXAMPLE 11

In a four-neck flask having an inner volume of 5 liters, 420 g of water was placed and the air entrapped in the flask was displaced with nitrogen gas. Then, the water and 1130 g of 2-dimethylthiazoline added thereto were stirred and heated at a temperature in the range of 40° to 60° C. and, in the meantime, adjusted to a pH value of 3.5 by dropwise addition thereto of 35 wt % hydrochloric acid over a period of about 4 hours. Then, the resultant reaction solution was heated under normal pressure to 120° C., then vacuumized to effect removal of acetone and water, reverted to normal pressure with nitrogen gas, and cooled to 80° C.

The molten cysteamine hydrochloride consequently obtained were aspired with a Pasteur pipet 2 mm in mouth diameter and dropped onto a tetrafluoroethylene plate having the opposite side thereof cooled with water to 30° C. The white solid cysteamine hydrochloride heaps consequently deposited on the plate were hemispheres 3 to 5 mm in diameter and 1 to 3 mm in height.

Samples of the cysteamine hydrochloride hemispheres obtained as described above were left standing at 30° C. for varying lengths of time, i.e. 0 to 30 days, and tested for solubility in an aqueous 35 wt % hydrochloric acid solution and ethanol and for susceptibility to agglomeration.

The results of the test for solubility are shown in Table 29 and those of the test for agglomeration in Table 30.

TABLE 29

| Number of days of standing | Time for solution (min) in aqueous 35 wt % HCl soln. | Time for solution (min) in ethanol |
|---|---|---|
| 0 | 2.5 | 32 |
| 7 | 2.6 | 34 |
| 14 | 2.6 | 33 |
| 30 | 2.5 | 32 |

TABLE 30

| Number of days of standing | Condition of motion |
|---|---|
| 0 | Absence of cohesion between particles |
| 7 | Absence of cohesion between particles |
| 14 | Absence of cohesion between particles |
| 30 | Absence of cohesion between particles |

CONTROL 5

In vials having the entrapped air therein displaced with nitrogen gas, samples of the same white crystalline cysteamine hydrochloride powder as obtained in Example 11 were left standing at 30° C. for varying lengths of time, i.e. 0 to 30 days, and tested in their undissolved state for solubility in an aqueous 35 wt % hydrochloric acid solution and ethanol and for susceptibility for agglomeration.

The results of the test for solubility are shown in Table 31 and those of the test for agglomeration in Table 32.

TABLE 31

| Number of days of standing | Time for solution (min) in aqueous 35 wt % HCl soln. | Time for solution (min) in N-ethyl-2-pyrrolidone |
|---|---|---|
| 0 | 2 | 22 |
| 7 | 24 | 68 |
| 14 | 30 | 74 |
| 30 | 36 | 84 |

TABLE 32

| Number of days of standing | Condition of motion |
|---|---|
| 0 | Absence of cohesion between particles |
| 7 | Agglomerated |
| 14 | Agglomerated |
| 30 | Agglomerated |

EXAMPLE 12

White solid cysteamine hydrochloride hemispheres 10 to 15 mm in diameter and 5 to 6 mm in height produced by following the procedure of Example 11 were tested for solubility in an aqueous 35 wt % hydrochloric acid solution and for susceptibility to agglomeration.

The results of the test for solubility are shown in Table 33 and those of the test for agglomeration in Table 34.

TABLE 33

| Number of days of standing | Time for solution (min) in aqueous 35 wt % HCl soln. |
|---|---|
| 0 | 5.7 |
| 7 | 5.8 |
| 14 | 5.6 |

TABLE 33-continued

| Number of days of standing | Time for solution (min) in aqueous 35 wt % HCl soln. |
| --- | --- |
| 30 | 5.7 |

TABLE 34

| Number of days of standing | Condition of motion |
| --- | --- |
| 0 | Absence of cohesion between particles |
| 7 | Absence of cohesion between particles |
| 14 | Absence of cohesion between particles |
| 30 | Absence of cohesion between particles |

EXAMPLE 13

Cysteamine hydrochloride powder was granulated by the use of a granulating device constructed as illustrated in FIGS. 2 and 3. To be more specific, the cysteamine hydrochloride powder was melted at a temperature of 72° C. with a melting device (not shown), kept substantially at this temperature and, at the same time, advanced through the conduit 15 kept at this temperature, and dropped by means of the dropping device 14 illustrated in FIG. 2 onto the belt conveyor 6 kept at a temperature of 25° C. thereby cooled and solidified, to produce granules having an average particle diameter in the range of 5 mm. In the meantime, the belt conveyor 6 had the lower side thereof cooled by causing ethylene glycol supplied from the cooling device 9 through the pump to be sprayed onto the lower side with the coolant spraying device 7. The ethylene glycol which had fulfilled its role of cooling the belt conveyor 6 was recovered by the recovering device 8 and returned to the cooling device 9, there to be cooled to the prescribed temperature. To the building 1 and the hopper 16, dry air was supplied through the conduits 17, 18 to keep the relative humidity inside them at 30%. The granules which were recovered in the hopper 16 had a water content of 0.1% by weight.

CONTROL 6

Granules having an average particle diameter of 2 to 5 mm were obtained by following the procedure of Example 1, excepting water was used as a coolant in the place of ethylene glycol. The granules had a water content of 0.7% by weight.

EXAMPLE 14

The procedure of Example 13 was repeated, except that a belt conveyor 16 of stainless steel having attached fast to the surface thereof through the medium of adhesive agent a tape 0.01 mm in thickness obtained by impregnating glass cloth with polytetrafluoroethylene was used as maintained at a temperature of 20° C. The granules which were recovered in the hopper 26 had a water content of 0.1% by weight. The belt conveyor showed no discernible sign of corrosion even after continued use.

EXAMPLE 15

Into a glass-lined reactor provided a stirrer, a thermometer and a condenser, 420 g of water and 1,170 g of 2-dimethyl thiazoline were charged, 38% by weight of hydrochloric acid was dropped for about 2 hours under maintaining 40° to 60° C. of a liquid temperature under stirring and pH of a reaction liquid was controlled to 3.0. The reaction liquid was elevated to temperature of 150° C. for about 10 hours under normal pressure and continuously distilling off dialkyl ketone which was by-produced during the reaction out of the reaction system, and the pressure was reduced to not more than 30 Torr and it was maintained 3 hours to remove water.

The molten cysteamine hydrochloride thus obtained was cooled down to a temperature of 80° C. advanced through the conduit 15 kept at this temperature, and dropped by means of the dropping device 14 illustrated in FIG. 2 onto the belt conveyor 6 of stainless steel coated with polytetrafluoroethylene of 10 μm of thickness kept at a temperature of 25° C. thereby cooled and solidified, to produce granules having an average particle diameter in the range of 5 mm. In the meantime, the belt conveyor 6 had the lower side thereof cooled by causing ethylene glycol supplied from the cooling device 9 through the pump to be sprayed onto the lower side with the coolant spraying device 7. The ethylene glycol which had fulfilled its role of cooling the belt conveyor 6 was recovered by the recovering device 8 and returned to the cooling device 9, there to be cooled to the prescribed temperature. To the building 1 and the hopper 16, dry air was supplied through the conduits 17, 18 to keep the relative humidity inside them at 30%. The granules which were recovered in the hopper 16 had a water content of 0.1% by weight iron content of not more than 1 ppm, and no color.

What is claimed is:

1. A method for the production of granular cysteamine hydrochloride having an average particle diameter in the range of 0.1 to 20 mm, comprising causing a powdery cysteamine hydrochloride to melt at a temperature of 68° to 150° C.; and dropping the molten cysteamine hydrochloride onto a corrosion-proof substrate maintained at a temperature of 10° to 40° C., thereby cooling and solidifying the drops of cysteamine hydrochloride.

2. A method according to claim 1, wherein said molten cysteamine hydrochloride is obtained by meltering cysteamine hydrochloride powder.

3. A method according to claim 1, wherein said molten cysteamine hydrochloride is obtained by synthesizing said cysteamine hydrochloride.

4. A method according to claim 1, wherein the granulation of said molten cysteamine hydrochloride is effected by cooling and solidification by the use of a plate type dropping granulating device.

5. A method according to claim 1, wherein said cysteamine hydrochloride is obtained by preparing cysteamine by the reaction of hydrogen sulfide with ethylene imine and causing the cysteamine to react with hydrochloric acid.

6. A method according to claim 5, wherein said cysteamine hydrochloride is obtained by keeping hydrogen sulfide under a pressure in the range of 6 to 10 kg/cm$^2$.G at a temperature in the range of 0° to 10° C. in the presence of a solvent and continuously adding ethylene imine thereto for reaction therewith, then heating the resultant reaction product to a temperature in the range of 60° to 70° C. thereby effecting separation of hydrogen sulfide therefrom, adding hydrochloric acid thereto, cooling the resultant mixture to a temperature not exceeding 5° C. thereby inducing precipitation of crystals.

7. A method according to claim 2, wherein said cysteamine hydrochloride powder is obtained by causing the sulfuric ester of 2-aminoethanol to react with carbon disulfide in the presence of an alkali hydroxide thereby forming 2-mercaptothiazoline and hydrolyzing the 2-mercaptothiazoline with hydrochloric acid.

8. A method according to claim 2, wherein said cysteamine hydrochloride powder is obtained by causing 2-aminoethyl sulfuric ester to react with sodium thiosulfate in the presence of an alkali hydroxide thereby forming S-(2-aminoethyl)thiosulfate and hydrolyzing the S-(2-aminoethyl)thiosulfate with hydrochloric acid.

9. A method according to claim 2, wherein said cysteamine hydrochloride powder is obtained by causing 20-chloroethyl chloroethyl amine hydrochloride to react with 2-mercaptothiazoline in the presence of a solvent thereby forming 2-(2'-aminoethylthio)-thiazolidine hydrochloride and hydrolyzing the 2-(2'-aminoethylthio)-thiazolidine hydrochloride.

10. A method according to claim 2, wherein said cysteamine hydrochloride powder is obtained by causing a 2-dialkylthiazoline to react with water and a halogenated hydroacid.

11. A method according to claim 3, wherein said cysteamine hydrochloride is obtained by adding hydrochloric acid in an amount of not less than equivalent amount to 2-dialkyl thiazolines represented by the formula I

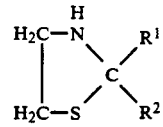

wherein $R^1$ and $R^2$ are independently at least one alkyl group selected from an alkyl group having 1 to 2 carbon atoms, in the presence of water under removing a by-produced dialkyl ketones continuously out of the reaction system, elevating a temperature to 130° to 160° C. to complete the reaction, and removing water in vacuo under maintaining 68° to 160° C.

12. A method for the production of granular cysteamine hydrochloride, which comprises granulating cysteamine hydrochloride by cooling and solidifying the molten cysteamine hydrochloride by the use of a plate type dropping granulating device and effecting required cooling of the cooling substrate of said plate type dropping granulating device by having the lower side of said substrate sprayed with a polyhydric alcohol-containing solution.

13. A method according to claim 12, wherein said polyhydric alcohol is ethylene glycol.

14. A method for the granulation of cysteamine hydrochloride, which comprises granulating cysteamine hydrochloride by cooling and solidifying the molten cysteamine hydrochloride by the use of a plate type dropping granulating device and effecting said cooling and solidifying by causing said molten cysteamine hydrochloride to fall in drops onto a metallic substrate formed by coating the surface of a cooling substrate of said plate type dropping granulating device with fluorine resin.

* * * * *